United States Patent [19]

Rosenberg et al.

[11] Patent Number: 5,531,598

[45] Date of Patent: Jul. 2, 1996

[54] PORTABLE ULTRASONIC DENTAL CLEANING DEVICE

[76] Inventors: Marvin Rosenberg, 125 Chateaux Dr., Palm Drive, Fla. 33480; Irving Wasson, Apartment 4F, 2000 S. Ocean Blvd., Boca Raton, Fla. 33432

[21] Appl. No.: 312,958

[22] Filed: Sep. 30, 1994

[51] Int. Cl.⁶ .............................. A61C 1/07; A61C 3/03; A61C 3/08
[52] U.S. Cl. ............................................ 433/119; 601/164
[58] Field of Search ...................... 433/86, 119; 601/164

[56] References Cited

U.S. PATENT DOCUMENTS

| | | |
|---|---|---|
| 3,401,690 | 9/1968 | Martin . |
| 3,651,576 | 3/1972 | Massa ................................... 433/119 |
| 4,071,956 | 2/1978 | Andress ................................. 433/119 |
| 4,127,125 | 11/1978 | Takemoto et al. .................. 433/119 X |
| 4,162,576 | 7/1979 | Takemoto et al. .................. 433/119 X |
| 4,176,454 | 12/1979 | Hatter et al. ............................. 433/119 |
| 4,192,035 | 3/1980 | Kuris . |
| 4,787,847 | 11/1988 | Martin et al. . |
| 5,138,733 | 8/1992 | Bock . |
| 5,314,333 | 5/1994 | Irmer et al. .......................... 433/119 X |

*Primary Examiner*—Nicholas D. Lucchesi

[57] ABSTRACT

An apparatus for the hygienic care of the teeth and surrounding gum tissue utilizes ultrasonic energy to massage and clean the teeth and gingival areas. A semi-rigid connector is provided for a handle, and a transducer provided with a liquid-filled membrane. The spring-action created by this handle would allow the transducer to contact the teeth. The transducer is configured to cover only a relatively small portion of the user's teeth and gingival tissue, and can easily be replaced.

5 Claims, 3 Drawing Sheets

PORTABLE ULTRASONIC DENTAL CLEANING DEVICE

BACKGROUND OF THE INVENTION

1. Field of the Invention

This invention relates to a portable ultrasonic dental cleaning device for stimulating the gums, and removing plaque and foreign substances from the surfaces of the teeth. The present invention has particular use in the home environment.

2. Description of the Prior Art

In the past, the use of ultrasonic energy as a cleansing device involved utilizing various unwieldy and cumbersome appliances which must directly contact the surface of the teeth in order to perform their proper function. Generally, this equipment could only be utilized in the office of a professional dentist, hygienist or similar practitioner, and produced some discomfort to the teeth or gums of a patient during its application. Furthermore, these prior art devices generally included a mouthpiece which was placed over the entire set of upper or lower teeth of the patient.

U.S. Pat. No. 3,401,690 issued to Martin et al, describes an ultrasonic cleaning device which is a slight improvement over the prior art, since only several teeth are cleansed at any one time. However, the dental cleaning device described in the Martin et al patent still suffers from the disadvantage that it must be employed in the office of a dental professional.

SUMMARY OF THE INVENTION

Deficiencies of the prior art are overcome by the present invention, which provides a portable, "over-the-counter" personal ultrasonic dental cleaning device which can be utilized in the home or any other convenient location. Furthermore, the present invention allows individuals to perform the cleaning function themselves without the assistance of a dental professional.

The present invention consists of a small, hand-held device which is applied to a selected, small group of the dentition, and moved along in sequence until a treatment has been completed.

The ultrasonic cleaning device is provided with a handle provided with a distal and proximal portion. A transducer is included in the proximal portion for converting electrical energy into the required mechanical energy. This mechanical energy is transferred to one or more teeth utilizing an applicator in the distal portion of the device. This applicator includes a liquid-filled membrane, provided with serrations on its outer surface to permit the applicator to adapt to various tooth sizes and configurations.

The applicator is spring-loaded which would allow it to cover the surfaces of the tooth/teeth, by firmly holding the handle portion, and with a light pressure, apply it to the tooth and gum surface by the user. Automatic adaptation to various tooth size and shape is provided.

Based upon the foregoing description of the invention, it is an object of the present invention to provide a hygienic device for the cleansing of the teeth and gum areas in the oral cavity.

It is another object of the present invention to provide an oral cleansing device for use in the home by a private individual.

Yet still another object of the present invention is to provide an apparatus and method for cleaning the teeth and gum areas, in which an ultrasonic transducer does not directly contact the teeth.

A further object of the present invention is to provide a hygienic device, and a method of using this device in which a medium, such as paste, may be used to help remove foreign substances from the teeth, while providing gum stimulation as well as freshening the mouth.

In accordance with these and other objects of the present invention, which will become apparent hereinafter, the instant invention will be described with particular reference to the accompanying drawings.

DETAILED DESCRIPTION OF THE PREFERRED EMBODIMENT

Figure 1:
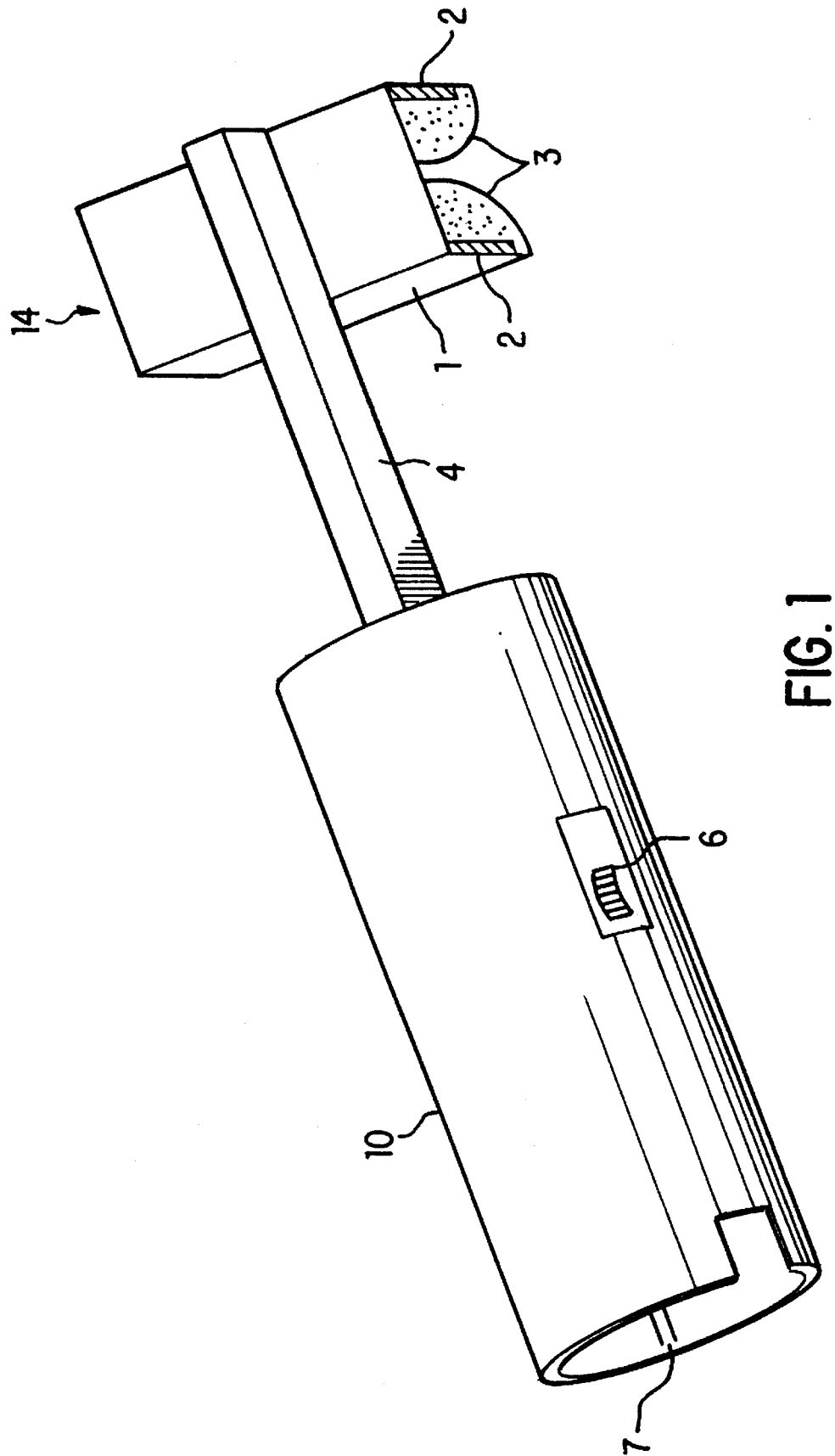
FIG. 1 shows a perspective side-view of the present invention.
Figure 2:
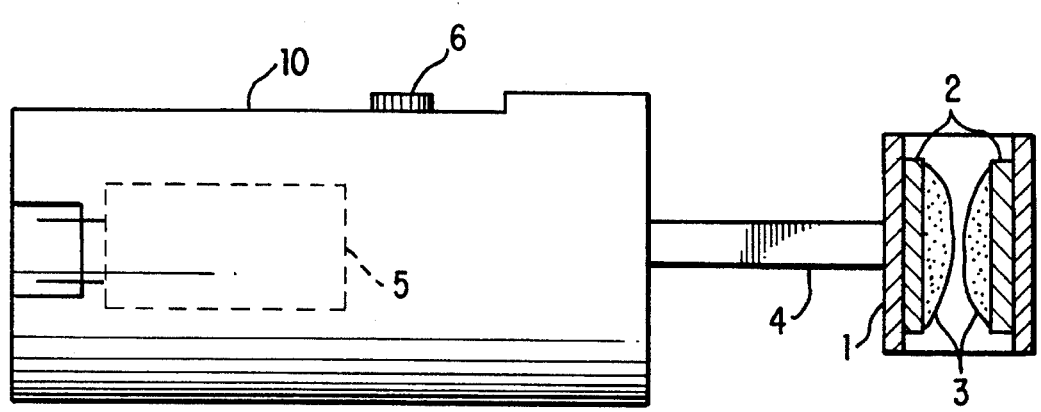
FIG. 2 shows a plan view of the present invention.
Figure 3:
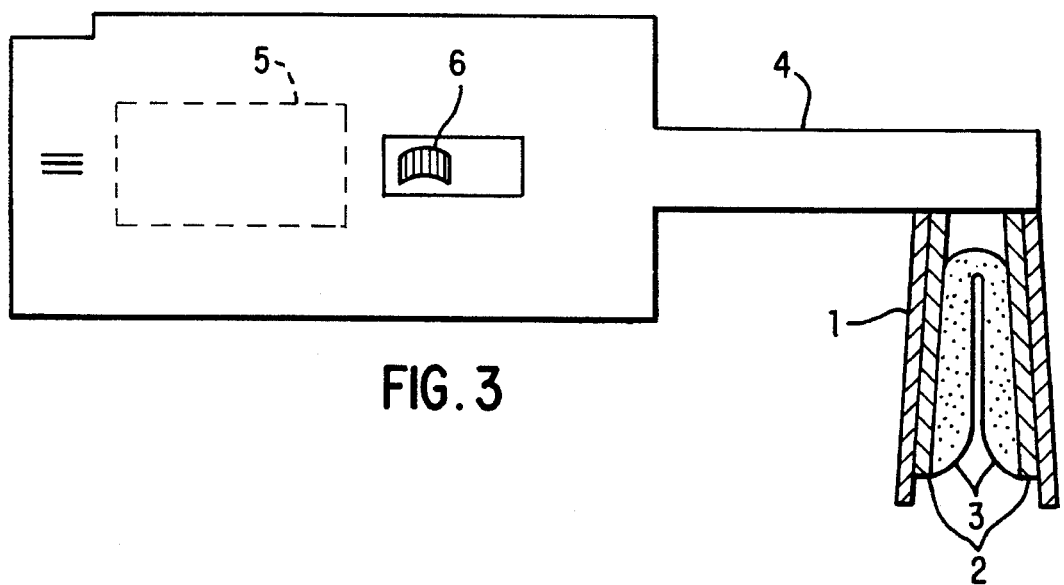
FIG. 3 is an elevational view of the present invention.

As shown in FIGS. 1, 2, and 3, the cleaning device, according to the present invention, is provided with a two-part housing/handle having a proximal portion and a distal portion. The proximal portion includes a cylindrical housing 10. The ultrasonic generator 2, powered by a standard source of battery power is located at the distal portion of the cleaning device. For example, as shown in FIGS. 1 and 2, a rechargeable battery 5 is used as the power source. This battery 5 is connected to outlet buttons 7. When not in use, the cleaning device is mounted and stored in a wall or sink mounted storage and recharging receptacle. This receptacle is connected to a standard wall outlet. The battery 5 is trickle charged by the charging equipment located in the receptacle. Charging and storage techniques are varied and well known in the art. A standard ON/OFF switch 6 is used to control to the operation of the dental cleaning device. The housing 10 is connected to an applicator through a semi-rigid connector 4, which forms the distal end of the two-part housing/handle.

The applicator portion 14 is provided with an exterior housing 1, a transducer 2, and a liquid-filled membrane 3. The housing 1, the transducer 2, and the membrane 3 will be biased inwardly to create a spring-like action utilizing ultrasonic energy. The membrane 3 is serrated, and the distal portion of the housing/handle 4 is much smaller in thickness than the proximal portion, and exhibits a rectangular shape in cross-section. Through the action of the ultrasonic generator significant stiffness is provided for vertical pressure on the teeth. The reduced thickness of the rectangular section in the lateral dimension provides for flexibility and optimum positioning in the selection of various dentine segments. The ultrasonic generator 2 is a typical quartz generator which vibrates as the relatively low voltage battery power, such as 12 volts D.C. is applied to it.

Various types of paste may be applied to the exterior of the membrane 3, which is filled with a liquid substance, such as water or a saline solution. The required mechanical action of the transducer 2 is translated to the sealed, liquid-filled membrane 3. The serrated surface of the membrane makes contact with the teeth and gums. The perpendicular and lateral scrubbing action generated by the present invention provides the required treatment.

The transducer 2 can be constructed of a known material, such as piezoelectric crystals, polarized ceramics, magnetos, trictive nickel, or other suitable materials which can operate at any suitable cleansing frequency.

Figure 4:
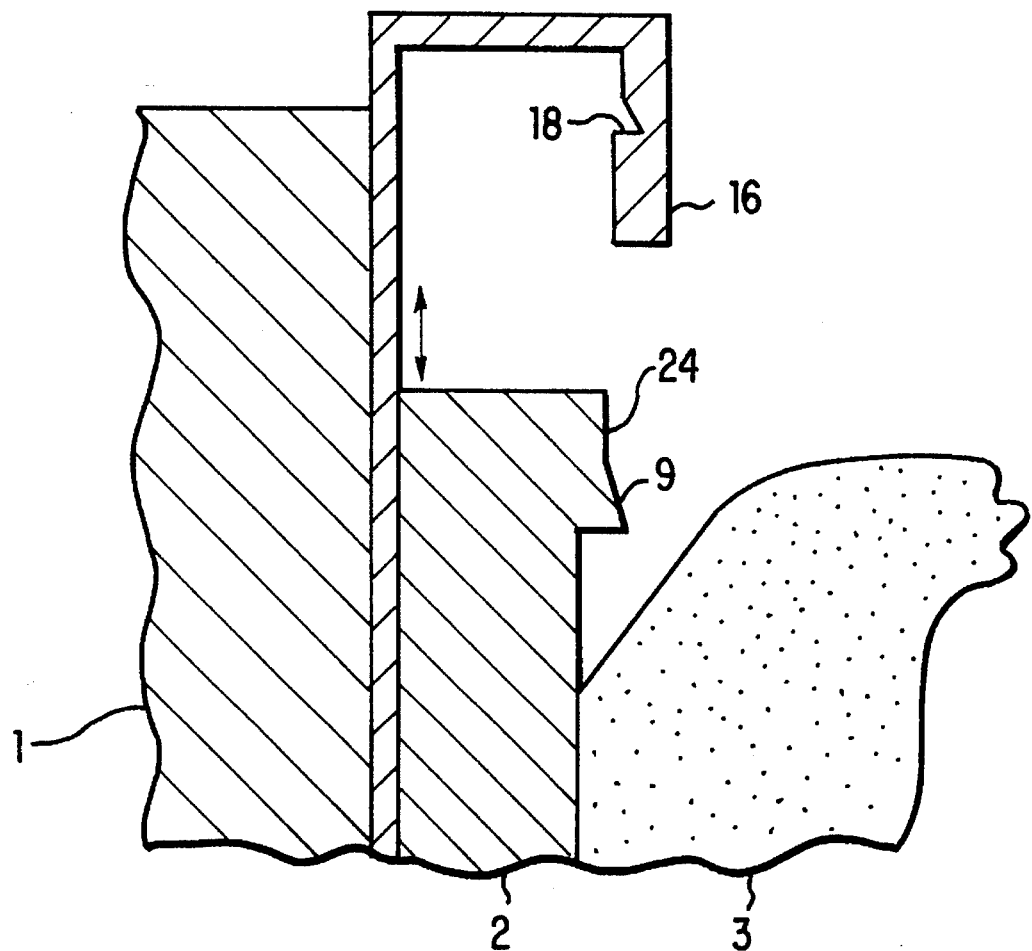
FIG. 4 is a cut-away view of the applicator portion of the present invention, showing a partially-replaced, membrane sub-assembly.

As shown in FIG. 4, the transducer 2 as well as the sealed liquid-filled membrane 3, can easily be replaced after a certain amount of usage. A wedge locking member 9 is provided on one of the outer surfaces 24 of transducer 2. A cutout or notched portion 18 is provided on the inner portion of lateral piece 16. Therefore, when the transducer 2 is inserted between pieces 16 and 18, the wedge 9, forces arm 16 aside to permit the wedge to lock into notch 18. At this time, the transducer 2 and the liquid-filled membrane 3 would be secured in place. It is noted that the transducer 2 and the membrane 3 can be removed, provided by the spring-action of the lateral piece 16.

In operation, paste is applied to the membrane 3. The applicator 14, including the transducer 2 is inserted into the mouth of the user and is applied to only a small section of the dentition. The spring-action of the semi-rigid distal portion 4 would provide the proper contact with the teeth. The switch 6 energizes the battery or other power source inside the handle 4, which provides the proper required power to the transducer 2. The paste on the membrane 3 is subjected to the motion which acts on the teeth and the gingival tissue areas. This stimulation removes plaque and other foreign particles from the teeth, and massages the gum areas without actually having the ultrasonic transducer physically contact the teeth and the gum areas. After completion of the treatment of the first selected area, the applicator 14 is moved along the teeth to the next application area. This procedure continues until all of the teeth have been treated. It is noted that due to the opposed nature of the applicator housing, either only a portion of the upper teeth or the lower teeth of the individual would be cleaned at any one time.

Although an illustrative embodiment of the invention has been described in detail herein, with reference to the accompanying drawings, it is to be understood that the invention is not limited to this precise embodiment. Various changes and modifications may be affected therein without the appliance of the scope or spirit of the invention. For example, although the drawings of the present invention show the applicator 14 directly affixed to the distal portion 4, this attachment can be made utilizing a swivel or rotary joint, thereby permitting automatic adjustment of angle between the portion 4 and the applicator 14. Additionally, the scrubbing action of the applicator can be produced by a transformer supplying power to an armature in a buzzer operation, instead of electronically.

What is claimed is:

1. A portable ultrasonic dental cleaning device, comprising:

a housing provided with a proximal section and a distal section, said proximal section provided with a cylindrical handle and including therein a source of electrical power, said distal section provided with a semi-rigid rectangularly shaped connector; and an applicator connected to said distal section, said applicator provided with an applicator housing, a transducer provided within said applicator housing and a closed liquid-filled membrane in direct contact with said transducer, said transducer provided with only first and second opposed members, said first and second opposed members configured and sized to cover only a portion of either the individual's top or bottom teeth when said applicator housing is inserted into the individual's mouth.

2. The portable ultrasonic dental cleaning device in accordance with claim 1, wherein said transducer and said liquid-filled membrane are removable from said applicator housing.

3. The portable ultrasonic dental cleaning device in accordance with claim 2, wherein said transducer is provided with a spring-biased wedge member mating with a notched portion provided in said applicator housing, to aid in removing said transducer and said liquid-filled membrane from said applicator housing.

4. The portable ultrasonic dental cleaning device in accordance with claim 1, wherein a source of electrical power is provided in said proximal section of said housing.

5. The portable ultrasonic dental cleaning device in accordance with claim 1, wherein said source of electrical power is a rechargeable battery.

\* \* \* \* \*